US006315949B1

(12) United States Patent
Carmello et al.

(10) Patent No.: US 6,315,949 B1
(45) Date of Patent: Nov. 13, 2001

(54) COMPOSITION FOR CARPET AND ROOM DEODORIZER AND METHOD OF DELIVERING THE COMPOSITION

(76) Inventors: Robert Carmello, 11 Highwood Dr., Dumont, NJ (US) 07628; Ernest Bernarducci, 209 Ridge Rd., Rutherford, NJ (US) 07070; Kenneth Ward, 220 Alexandria Way, Basking Ridge, NJ (US) 07920; Isabel Lopes, 11 Falcon Rd., Livingston, NJ (US) 07039; Karen Mack, 10442 E. Mercer La., Scottsdale, AZ (US) 85259

(*) Notice: Subject to any disclaimer, the term of this patent is extended or adjusted under 35 U.S.C. 154(b) by 0 days.

(21) Appl. No.: 09/476,216

(22) Filed: Dec. 30, 1999

(51) Int. Cl.[7] ............... A61L 9/04; A61L 9/012; A61L 9/013
(52) U.S. Cl. ............... 422/5; 424/43; 424/76.2; 424/725; 512/5
(58) Field of Search .................. 422/5; 424/43, 424/76.2, 76.9, 725; 512/5

(56) References Cited

U.S. PATENT DOCUMENTS

| | | | |
|---|---|---|---|
| 3,779,929 | 12/1973 | Abler | 252/90 |
| 3,915,902 | 10/1975 | Ancel | 252/526 |
| 3,919,101 | 11/1975 | Anstett | 252/90 |
| 3,994,744 | 11/1976 | Anderle | 134/4 |
| 4,552,692 | 11/1985 | Gillespie | 252/528 |
| 4,652,389 | 3/1987 | Moll | 252/90 |
| 4,816,220 | 3/1989 | Roychowdhury . | |
| 4,931,204 | 6/1990 | Ramirez | 252/167 |
| 5,352,437 | 10/1994 | Nakagawa | 424/45 |
| 5,663,134 | 9/1997 | Trinh | 510/406 |
| 5,665,332 | 9/1997 | Mundschenk et al. . | |
| 5,670,475 | 9/1997 | Trinh | 510/470 |
| 5,679,324 | 10/1997 | Lisboa et al. . | |
| 5,853,618 | 12/1998 | Barker | 252/321 |
| 5,906,992 | 5/1999 | Fonsny et al. . | |

FOREIGN PATENT DOCUMENTS

1321579-A * 7/1973 (GB) .

* cited by examiner

Primary Examiner—Elizabeth McKane
(74) Attorney, Agent, or Firm—Bazerman & Drangel, PC

(57) ABSTRACT

A composition for deodorizing and refreshing surfaces such as carpets, upholstery, furniture etc. The composition disclosed is a highly friable foam that rapidly evaporates upon contact with the surface to be refreshed. Therefore, the composition does not require removal by vacuuming after application to the surface. A method for using the composition to deodorize and refresh a surface is also disclosed.

21 Claims, No Drawings

COMPOSITION FOR CARPET AND ROOM DEODORIZER AND METHOD OF DELIVERING THE COMPOSITION

BACKGROUND OF THE INVENTION

The present invention is directed to a novel composition for a carpet deodorizer and a novel method for delivering the same to a carpet. Even when carpets are clean, the carpet can become malodorous from everyday smells that are present in the home or office such as pet odors, cigarette smoke, cooking smells etc. Thus, carpet deodorizers or refreshers are used to remove these odors during the relatively long time periods between cleanings.

The presently available compositions for carpet deodorizers are generally in the form of a powder that is sprinkled onto the carpet. The powder is left on the carpet for a short period of time, i.e., approximately 5 minutes. The powder must then be removed from the carpet typically by vacuuming. The process of vacuuming the powder causes the room to be deodorized and a small amount of residual powder remains on the carpet causing the carpet to be deodorized. If the powder is not removed from the carpet, it can potentially damage or stain the carpet. In addition, the presently available carpet deodorizers cannot be used if the area of the carpet requiring deodorizing is wet or damp since the powder would mix with the moisture and be difficult to vacuum from the carpet.

The presently available compositions suffer from other disadvantages as well. First, if the powder compositions are used repeatedly, the powder tends to sift down through the carpet and backing and onto the floor beneath the carpet. When this occurs, the powder can damage or stain the wood floor beneath the carpet.

One object of the present invention is to provide a composition for a carpet deodorizer that does not require removal from the carpet by vacuuming after application. Another object of the present invention is to provide a novel method of application of a carpet deodorizer so that the difficulties associated with the need to remove the carpet deodorizer are ameliorated. Another object of the present invention is to provide a carpet deodorizer composition that may applied to the carpet surface regardless of whether the carpet is wet or damp. Another object of the present invention is to provide a carpet deodorizer that does not sift down through the carpet and damage the underlying floor. Another object of the invention is to provide a quick method of deodorizing a carpet that does not require the time consuming step of removing the carpet deodorizer by vacuuming.

SUMMARY OF THE INVENTION

The present invention is directed to a composition and method that solves the problems associated with prior compositions and methods for deodorizing and refreshing foul smelling surfaces covered with some sort of fabric such as carpets, upholstery, etc. The present invention is directed to a highly-friable foam composition that rapidly evaporates upon contact with the surface to be deodorized or refreshed. Due to the rapid evaporation of the composition, the composition does not require removal from the surface by vacuuming.

The composition, in its simplest form, comprises an aromatic essential oil to provide fragrance, a surface-active agent and deionized water. Other ingredients may optionally be added such as anti-foaming agents, a solvent, an anti-redeposition agent, a corrosion inhibitor and a pH adjuster.

DETAILED DESCRIPTION OF THE INVENTION

The present invention is directed to a novel carpet and room deodorizing composition 10 as well as a novel means of delivering the composition to the carpet. The composition 10 of the present invention dissipates rapidly upon contact with the fibers of the carpet. Consequently, the composition 10 does not require removal by vacuuming after application.

The composition 10 of the present invention is directed to a non-powder form of a carpet and room deodorizer. The composition 10 is delivered to the carpet by either aerosol means or by atomization. Upon contact with the carpet fibers, a highly-friable foam is observed. The foam rapidly dissipates by evaporation within seconds of delivery to the carpet. The highly-friable foam that is produced simulates the effect of the prior powder form of carpet deodorizers in that small foam droplets ranging from loose to dense bubbles are formed on the carpet fibers. The rapid evaporation of the composition 10 eliminates the need to remove the composition 10 by vacuuming after application to the carpet.

A further extension of the use of the composition 10 of the present invention is to extend the use of the composition 10 to other fabric surfaces in addition to carpets. Since the composition 10 of the present invention does not require removal by vacuuming, the composition 10 may be more readily applied than the presently available carpet deodorizers to other areas of the home or office such as upholstery, furniture, bedding, cat litter boxes, pet sleeping areas etc.

The composition 10 of the present invention is an aqueous medium that comprises an aromatic essential oil 12 for fragrance, a surface active agent 14, an anti-foam agent 16, a solvent 18, an anti-redeposition (anti-resoiling) agent 20, a corrosion inhibitor 24, a pH adjuster 26 and deionized water 28. The surface-active agent 14 is intended to produce a foaming action of the composition 10 when applied to the carpet. The anti-foam agent 16 enables fast breaking action of the foam upon delivery to the carpet. The solvent 18 is utilized as a formulation aid and also to enable faster evaporation of the composition 10 upon contact with the carpet. The anti-redeposition agent 20 acts to prevent soiling of the carpet by the composition 10, i.e. prevents the small amount of composition 10 left on the carpet from attracting dirt. The fragrance 12 is the active ingredient that delivers freshening, deodorizing, and neutralizing efficacy to the treated carpet or other surfaces.

The preferred embodiment of the composition 10 of the present invention is set forth in the following table:

TABLE I

| INGREDIENT | FUNCTION | PERCENT BY WEIGHT |
| --- | --- | --- |
| 1) Sodium Lauryl Sarconsinate 30% | Surfactant & Foaming Agent | 1.27 |
| 2) Carboxylated Fluoro Polymer Salt | Antiredeposition Agent | 0.90 |
| 3) Silicone Antifoam Emulsion | Antifoam | 0.50 |
| 4) Isopropyl Alcohol | Solvent and Antifoam | 2.50 |
| 5) Fragrance | Freshener & Deodorizer | 1.00 |
| 6) Triethanolamine, 85% | pH Adjuster & Corrosion Inhibitor | 0.10 |
| 7) Sodium Benzoate | Corrosion Inhibitor | 0.20 |
| 8) Deionized Water | Solubilizer Base | 93.53 |

The following Table II indicates the approximate allowable ranges for the components set forth in Table I;

TABLE II

| INGREDIENT | ALLOWABLE RANGE OF PERCENT BY WEIGHT |
| --- | --- |
| 1) Sodium Lauryl Sarconsinate 30% | 0.5 to 6.00% |
| 2) Carboxylated Fluoro Polymer Salt | 0.00 to 3.00% |
| 3) Silicone Antifoam Emulsion | 0.00 to 2.00% |
| 4) Isopropyl Alcohol | 0 to 5.00% |
| 5) Fragrance | 0.05 to 5.00% |
| 6) Triethanolamine, 85% | 0.00 to 2.00% |
| 7) Sodium Benzoate | 0.00 to 2.00% |
| 8) Deionized Water | 75.00 to 99.45% |

If the amount of Sodium Lauryl Sarcosinite, 30% exceeds the above range carpet resoiling would occur. In addition, the resulting foam would be too dense to rapidly evaporate and thus potentially defeat the object of the present invention. The Sodium Lauryl Sarconsinite also aids in the solubilization of the fragrance oil. As indicated in Table II, the Carboxylated Fluoro Polymer Salt may not be required under certain circumstances. Such circumstances would be a compound comprising a low level of the Surface Active Agent 14. The Silicone Antifoam Emulsion is likewise not necessarily required when a low level of the Surface Active Agent 14 is utilized. It should also be noted that those of ordinary skill in the art will recognize that the antifoam agent is not limited to silicone emulsions but other equivalent antifoaming agents may be utilized as well.

The isopropyl alcohol aids in breaking down the foam, aids in solubilization of the fragrance oil 12 and also promotes lifting of the fragrance into the ambient air above the surface to be treated with the composition 10. As indicated in Table II, the isopropyl alcohol is not required in certain circumstances. Such circumstances would be a compound comprising high levels of the surface-active agent 14, the antifoam 16 and the fragrance 12.

The fragrance 12 acts as a deodorizer. If the fragrance 12 were present in an amount below the range set forth in Table II, the fragrance 12 would not be effective in providing a deodorizing effect. A level of fragrance 12 higher than the range set forth in Table II would result in carpet resoiling. In addition, the effect of the fragrance 12 may become overpowering if the range set forth in Table II is exceeded.

The triethanolamine 85% and the sodium benzoate are used to inhibit corrosion in aerosol containers that have an internal surface comprising tin plating. If an aluminum or other type of container is used, neither the triethanolarnine 85% nor the sodium benzoate is required.

The percent amount of water in the composition 10 is based on the upper and lower ranges of the other components. Thus, the range set forth in Table II is a result of the percentage of the other components comprising the composition 10.

The composition 10 as particularly set forth in Table I or Table II will be packaged with a propellant in a conventional aerosol spray delivery container. In the preferred embodiment the propellant is A-46 (Isobutane/Propane) however, any of the conventional aerosol propellants known to those of ordinary skill in the art may be substituted. The composition as set forth in Table I comprises 75% of the mixture in the aerosol spray delivery container with the propellant comprising 25% by weight of the final mixture. Those of ordinary skill in the art will recognize that the precise ratio of composition 10 to propellant in the final product may be varied greatly without departing from the spirit or scope of the present invention. For example, it is contemplated that the propellant could vary from 60% to 96% of the final mixture with the composition 10 varying inversely from the propellant from 40% to 4%.

As an alternative to delivery by means of an aerosol spray, the composition 10 set forth in Table I may atomized. A foam may be achieved by atomization by mixing the composition 10 with surfactants such as sulfosuccinates, sarcosinates and sodium lauryl sulfate. The atomized foam will be delivered by means of a mechanical trigger spray device. The trigger spray device provides for mechanical break up of the foam particles upon delivery to the carpet. In an alternative embodiment of the present invention, a malodor counteractant and or a neutralizing agent may be incorporated with the fragrance 12.

The composition 10 is delivered to the carpet or other surface by spraying from either the aerosol spray container or the mechanical trigger spray device. The composition 10 rapidly forms a foam upon contact with the carpet fibers or other surface to be deodorized. The foam is highly friable and dissipates within seconds of application to the surface by means of evaporation. Within approximately 5 minutes, the carpet is dry. There is no need to remove any residue from the composition by vacuuming since only a minor and invisible amount of the composition 10 is left behind on the carpet after approximately 5 minutes. However, the effect of the composition 10 is to remove any odors from the carpet or other surface as well as leaving a fresh smell in the entire room in which the composition may be applied.

Those of ordinary skill in the art will recognize that the embodiments just described merely illustrate the principles of the present invention. Many modifications may be made thereto without departing from the spirit and scope of the invention as set forth in the following claims.

What is claimed is:

1. A composition for deodorizing and refreshing a surface comprising:
   a) an aromatic essential oil for fragrance;
   b) a surface active agent;
   c) water; and
   d) a non-surfactant anti-redeposition agent
      wherein the composition forms a friable foam upon contact with the surface and rapidly evaporates therefrom.

2. The composition of claim 1 further comprising:
   a) an anti-foam agent; and
   b) a solvent.

3. The composition of claim 2 wherein:
   a) the anti-foam agent comprises silicone antifoam emulsion;
   b) the solvent comprises isopropyl alcohol; and
   c) the anti-redeposition agent comprises carboxylated fluoro polymer salt.

4. The composition of claim 3 wherein:
   a) the aromatic essential oil comprises 0.05 to 5.00% by weight of the composition;
   b) the surface active agent comprises 0.5 to 6.0% by weight of the composition;
   c) the anti-foam agent comprises 0% to 2.0% of the composition by weight;
   d) the solvent comprises 0% to 5% by weight of the composition;
   e) the anti-redeposition agent comprises 0 to 3% by weight of the composition; and f) the water comprises 75% to 99.45% by weight of the composition.

5. The composition of claim 3 wherein:
a) the aromatic essential oil comprises about 1.00% by weight of the composition;
b) the surface active agent comprises about 1.27% by weight of the composition;
c) the anti-foam agent comprises about 0.5% of the composition by weight;
d) the solvent comprises about 2.5% by weight of the composition;
e) the anti-redeposition agent comprises about 0.90% by weight of the composition; and
f) the water comprises about 93.53% by weight of the composition.

6. The composition of claim 2 further comprising:
a) a corrosion inhibitor; and
b) a pH adjuster.

7. The composition of claim 6 further wherein:
a) the corrosion inhibitor comprises sodium benzoate and triethanolamine, 30%; and
b) The pH adjuster comprises triethanolamine 30%.

8. The composition of claim 7 wherein:
a) the corrosion inhibitor comprises 0% to 2% by weight of the composition; and
b) the pH adjuster comprises 0% to 2% by weight of the composition.

9. The composition of claim 7 wherein:
a) the corrosion inhibitor comprises about 0.2% by weight of the composition; and
b) the pH adjuster comprises about 0.2% by weight of the composition.

10. The composition of claim 1 wherein:
a) the surface active agent comprises sodium lauryl sarcosinate, 30%.

11. The composition of claim 10 wherein:
a) the aromatic essential oil comprises about 1.0% by weight of the composition;
b) the surface active agent comprises about 1.27% by weight of the composition;
c) the water comprises about 97.73% by weight of the composition.

12. The composition of claim 1 wherein:
a) the aromatic essential oil comprises 0.05% to 5.0% of the composition by weight;
b) the surface active agent comprises 0.5% to 6.0% of the composition by weight; and
c) the water comprises 89% to 99.45% of the composition by weight.

13. The composition of claim 12 wherein;
a) surface active agent comprises sodium lauryl sarcosinate 30%.

14. A mixture comprising the composition of claim 1, 2, 3, 4, 5, 10, 11, 12, or 13 and an aerosol propellant.

15. The mixture of claim 14 wherein the composition comprises 75% of the mixture by weight and the propellant comprises 25% of the mixture by weight.

16. The method for deodorizing and refreshing fabrics, carpets, rugs and upholstery comprising the following steps:
a) mixing a friable foam composition, wherein the composition comprises an aromatic oil, a surface active agent, an anti-redeposition agent and water, with a propellant;
b) packaging the mixture under pressure in an aerosol spray container;
c) spraying the composition from the aerosol container onto a fabric, carpet, rug or upholstery; and
d) evaporating primarily all of the composition from the fabric, carpet, rug or upholstery.

17. The method of claim 16 wherein:
a) the surface active agent comprises sodium lauryl sarcosinate, 30%.

18. The method of claim 17 wherein the friable foam composition further comprises:
a) an anti-foam agent; and
b) a solvent.

19. The method of claim 18 wherein:
a) the anti-foam agent comprises silicone antifoam emulsion;
b) the solvent comprises isopropryl alcohol; and
c) the anti-redeposition agent comprises carboxylated fluoro polymer salt.

20. The method of claim 16 wherein the anti-redeposition agent is not a surface active agent.

21. A composition for deodorizing and refreshing fabric, carpets, rugs and upholstery comprising:
a) an aromatic essential oil for fragrance;
b) a surface active agent;
c) water; and
d) a non-surface active agent anti-redeposition agent wherein the composition forms a friable foam upon contact with a fabric, carpet, rug or upholstery and rapidly evaporates therefrom.

\* \* \* \* \*